United States Patent [19]

Lovestedt

[11] Patent Number: 5,346,487
[45] Date of Patent: Sep. 13, 1994

[54] DISPOSABLE ABSORBENT GARMENT

[75] Inventor: Penny C. Lovestedt, Renton, Wash.

[73] Assignee: Paragon Trade Brands, Inc., Federal Way, Wash.

[21] Appl. No.: 68,505

[22] Filed: May 26, 1993

[51] Int. Cl.5 .................. A61F 13/15; A61F 13/20
[52] U.S. Cl. .................. 604/385.1; 604/358; 604/369; 604/378; 604/393
[58] Field of Search ............ 604/358, 369, 378, 385.1, 604/373, 381, 382, 385.2, 393, 396, 397, 398

[56] References Cited

U.S. PATENT DOCUMENTS

| | | |
|---|---|---|
| 3,349,769 | 10/1967 | Piekarski . |
| 3,572,342 | 3/1971 | Lindquist et al. . |
| 4,425,127 | 1/1984 | Suzuki et al. ............ 604/369 |
| 4,578,066 | 3/1986 | O'Connor . |
| 4,610,682 | 9/1986 | Kopp . |
| 4,695,278 | 9/1987 | Lawson . |
| 4,726,807 | 2/1988 | Young et al. . |
| 4,743,246 | 5/1988 | Lawson . |
| 4,804,379 | 2/1989 | Toth et al. . |
| 4,885,204 | 12/1989 | Bither et al. . |
| 4,892,528 | 1/1990 | Suzuki et al. . |
| 4,900,318 | 2/1990 | Toth . |
| 4,917,682 | 4/1990 | Lancaster et al. . |
| 4,936,840 | 6/1990 | Proxmire ............ 604/385.2 |
| 4,938,755 | 7/1990 | Foreman ............ 604/385.1 |
| 4,978,570 | 12/1990 | Heyn et al. ............ 604/369 |
| 4,988,344 | 1/1991 | Reising et al. . |
| 5,013,382 | 5/1991 | Nalowaniec et al. . |
| 5,021,050 | 6/1991 | Iskra . |
| 5,026,364 | 6/1991 | Robertson ............ 604/385.1 |
| 5,064,421 | 11/1991 | Tracy ............ 604/385.1 |
| 5,188,626 | 2/1993 | Toyada et al. ............ 604/358 |

Primary Examiner—Randall L. Green
Assistant Examiner—P. Zuttarelli
Attorney, Agent, or Firm—Klarquist, Sparkman, Campbell, Leigh & Whinston

[57] ABSTRACT

A disposable absorbing garment having a liquid impervious back sheet with waist regions and a crotch region therebetween. An elongate waistband extends along the waist region of the back sheet, an absorbent pad overlies the crotch region of the back sheet with end edges at the pad spaced inwardly from the waistband, and a liquid pervious liner sheet overlies the pad with its end margins wrapped around the ends of the pad. A hydrophobic extension sheet extends between the pad and waistband, with a first portion overlying the waistband and a second portion between the pad and back sheet. A method for assembly of such a garment includes the steps of forming a liquid impervious back sheet with laterally extending waist regions and a crotch region therebetween, attaching an elongate waistband to the inner side of a waist region, placing a portion of a hydrophobic extension sheet over the waistband with remainder portions of the extension sheet extending toward the crotch region, providing an absorbent pad between the opposed waist regions of the back sheet, overlying one face of the pad with a liquid pervious liner sheet and wrapping end margins of the liner sheet around the opposite edges of the pad and securing the combined pad and liner sheet to the back sheet with the end edges of the pad spaced inwardly from the waistband and overlying a portion of the extension sheet.

20 Claims, 1 Drawing Sheet

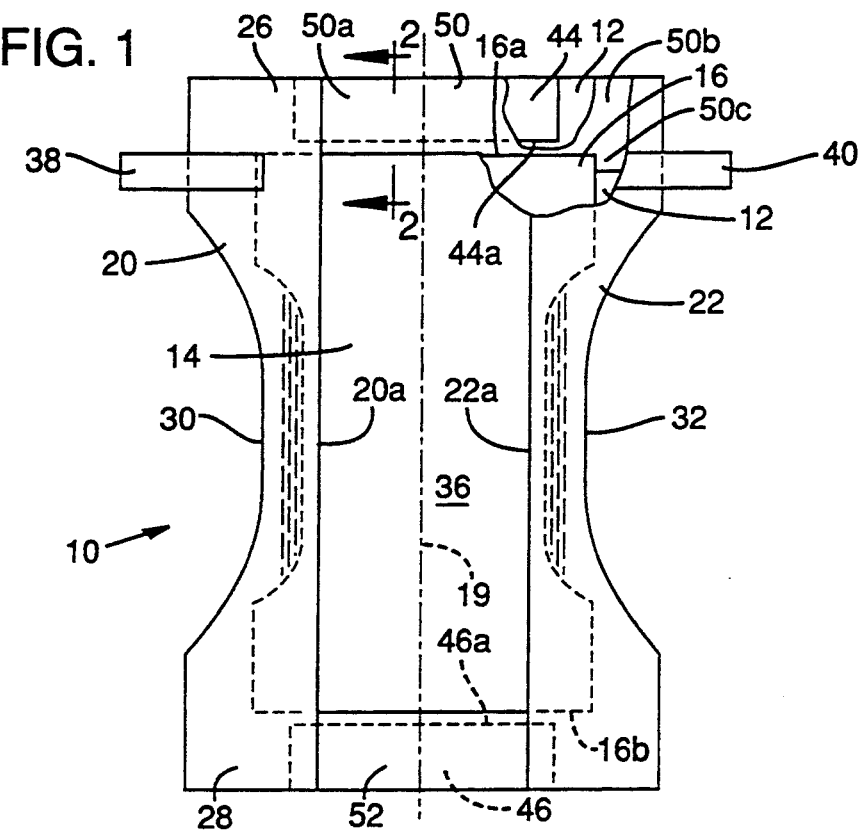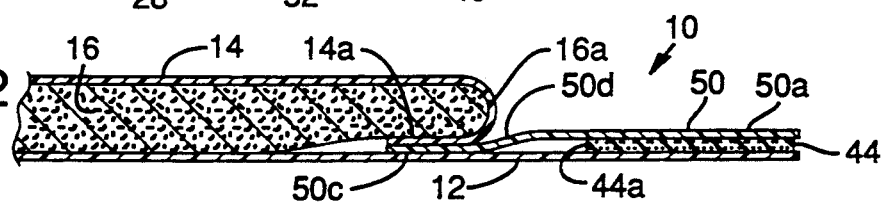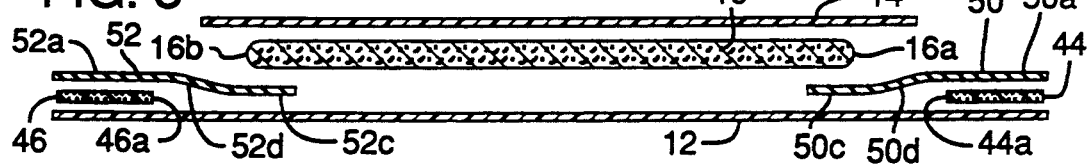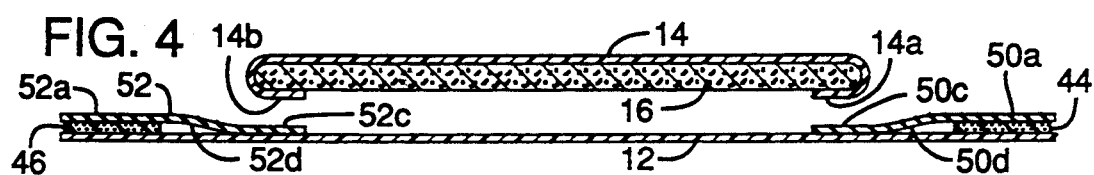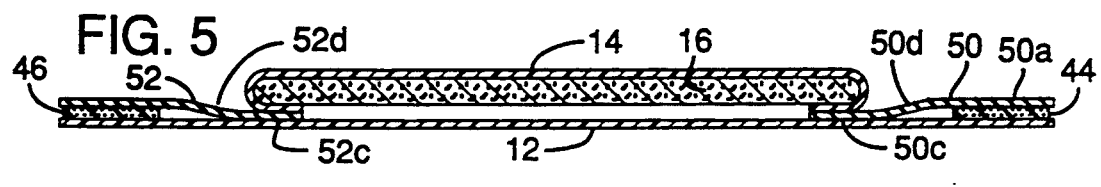

DISPOSABLE ABSORBENT GARMENT

BACKGROUND OF THE INVENTION

The present invention relates generally to a disposable absorbent garment, such as a diaper, and more specifically to such a garment which is constructed to minimize leakage at the waist region of the garment.

The primary function of disposable absorbent garments, such as disposable diapers and adult incontinent briefs, is to absorb and contain body exudates. Although they are intended to prevent exudates from leaking from the interior of the garment, leakage around various parts of the product where it contacts the wearer often has occurred. Of particular concern is leakage of liquids from the waist regions.

These problems have been the subject of a great deal of activity in the past in an attempt to prevent leakage at the waist region of a disposable absorbent garment. Such prior activity has not provided entirely satisfactory solutions to the problem of waist leakage.

An object of the present invention is to provide an improved disposable absorbent garment which has improved containment characteristics at the waist region.

It is a further object of the present invention to provide such a novel disposable absorbent garment which is economical to manufacture.

A further object of the present invention is to provide a disposable absorbent garment which minimizes leakage around the waist edges thereof and which thereby prevents escaping of moisture to outer garments of the wearer.

More specifically, it is an object of the present invention to provide an absorbent garment having a hydrophobic extension sheet extending between the underside of an absorbent pad and a hydrophobic backing sheet to a region overlying a waistband region on the garment to inhibit transmission of liquid laterally from the absorbent pad outwardly toward the waist region of the garment.

A further object of the present invention is to provide a novel method for constructing a disposable absorbent garment which is easily and economically accomplished, and provides a garment which minimizes leakage at the waistband region of the garment.

In accordance with the present invention, an integral disposable absorbent garment is provided which includes a liquid impervious back sheet, an elongate waistband secured to and extending along the inner side of a waist region of the back sheet, an absorbent pad overlying the inner side of the crotch region of the back sheet with an end edge of the pad spaced inwardly from the waistband, a liquid pervious liner sheet overlying the pad and having an end margin portion wrapped around the end edge of the pad, and a hydrophobic extension sheet extending between the pad and waistband having a first portion overlying the waistband and a second portion interposed between the pad and back sheet.

Also in accordance with the present invention, a method is provided for producing a disposable absorbent garment which includes the steps of forming a liquid impervious back sheet having opposed, laterally extending waist regions and an intermediate crotch region, attaching an elongate waistband to the inner side of a waist region of the back sheet, placing a portion of a hydrophobic extension sheet over the waistband with remainder portions of the extension sheet extending toward the crotch region of the back sheet, providing an absorbent pad having a length shorter than the distance between the opposed waist regions of the back sheet, overlying the face of the pad with a liquid pervious liner sheet with end margin portions of the liner sheet wrapping around an end edge of the pad and terminating adjacent the opposite face of the pad, and securing the combined pad and liner sheet to the crotch region of the inner face of the back sheet with the wrapped end edge of the pad spaced inwardly from the waistband and overlying a portion of the extension sheet.

When a diaper constructed according to the invention is applied to a wearer, the extension sheet inhibits transmission of liquids laterally from the pad toward the waist region of the diaper to improve containment within the garment to minimize leakage at the waist region of the garment.

BRIEF DESCRIPTION OF THE DRAWINGS

FIG. 1 is a plan view of a disposable absorbent garment according to an embodiment of the present invention having portions broken away to reveal underlying structure;

FIG. 2 is an enlarged cross-sectional view taken generally along the line 2—2 in FIG. 1;

FIGS. 3, 4 and 5 are simplified side elevation views of successive steps in a method for producing a disposable absorbent garment according to the invention.

DETAILED DESCRIPTION

FIG. 1 illustrates an embodiment of a disposable absorbent garment 10 manufactured in accordance with the invention having a liquid impervious outer layer, or back sheet, 12, and a liquid pervious body-contacting inner layer, or top sheet, 14, often referred to as a liner sheet, or top sheet. A moisture absorbent fluff filler pad layer, or core, 16 is sandwiched and encased between back sheet 12 and liner sheet 14. The garment is substantially symmetrical on opposite sides of its longitudinal axis 19.

A pair of liquid impervious side sheets 20, 22 are secured adjacent their inner marginal edge portions 20a, 22a to liner sheet 14, as by the application of lines of hot melt adhesive therebetween. Side sheets 20, 22 extend laterally outwardly from liner sheet 14 to be coterminous with and are secured to the outer side margins of back sheet 12.

The disposable absorbent garment 10 typically is used as a baby or infant diaper, or as an adult incontinence brief. The general manufacture of such garments are well-known in the art. One garment and method of manufacture is illustrated in U.S. Pat. No. 4,726,807 to Richard H. Young and Peter Lancaster, which is herein incorporated by reference to illustrate typical materials used and methods of manufacturing such garments.

For example, the liquid impervious back sheet 12 may be of a thin thermoplastic material, such as a pigmented polyethylene film having a thickness in the range of 0.02–0.04 mm. The liquid pervious liner sheet may be a carded polyester fiber with a latex binder or of a spun-bonded polypropylene having continuous fibers and thermally bonded by patterned calendar rolls. The liner sheet may be impregnated with a surfactant to render it hydrophilic. The moisture absorbent layer, or pad, 16 may be of wood fibers or other fibers, such as chemical wood pulp, or any other suitable liquid absorbing material such as commercially available fluff pulp or of a fluffed bleached craft soft wood pulp.

The garment has opposed transverse waist regions 26, 28 disposed to lie along the front and rear waist areas of a wearer. Opposed in-cut side margins 30, 32 provide a somewhat hourglass shape to the garment. When the garment is fitted on a wearer the opposed side margins 30, 32 define leg-encircling openings, waist region 26 contacts the rear waist area of a user, and waist region 28 contacts the wearer's front waist region. Lying between the opposed side margins 30, 32 and waist regions 26, 28 is a crotch region 36 which is substantially central to the garment.

The absorbent pad 16 has a substantially hourglass shape configuration also, but is of a smaller dimension than the side-to-side and end-to-end dimensions of back sheet 12 and side margins 30, 32, such that marginal side edge portions and end portions are provided on the garment which are free of the absorbent pad. Outer edge margin portions of side sheets 20, 22 may be secured to outer marginal edge portions of back sheet 12 as by the application of hot melt glue therebetween to bond them together and encase pad 16 therebetween.

A pair of adhesive tabs 38, 40 are secured to waist region 26 of back sheet 12 and extend outwardly therefrom. When the garment is placed on the user the outwardly extending portions of these adhesive tabs may be adhered to back sheet 12 in waist region 28 to provide an enclosing absorbent garment for the user.

An elongate elasticized waistband 44 extends transversely of the longitudinal axis of the diaper and is secured, as by appropriate adhesives, to the inner side of back sheet 12 in waist region 26 of the diaper. The waistband may be an elastic cushioning foam piece, such as may be supplied by Woodbridge Foam Company, which is approximately 1.8 mm thick before stretching. It is capable of being stretched to 1.5 to two times its length and is thus stretched prior to applying to the back sheet 12. The foam piece is applied to the back sheet in its stretched condition and adhered thereto, as by the use of hot melt adhesives. A similar waistband piece 46 is stretched and secured to the opposite waist region 28 of back sheet 12, extending transversely of the garment. Upon release the waistband pieces contract to produce elasticized waist regions for the garment.

As is seen in FIGS. 1 and 2, pad 16 is shorter than the distance between the opposed inner edges 44a, 46a of waistband pieces 44, 46. Thus the outer end edges 16a, 16b of the pad are spaced inwardly a distance from the inner edges 44a, 46a of the waistband pieces.

Referring to FIGS. 2 and 4, liner sheet 14 has opposite end margin portions, indicated generally at 14a, 14b, which are wrapped around end edges 16a, 16b of the pad and terminate between the pad and back sheet 12.

An elongate hydrophobic extension sheet 50 is disposed at one waist region 26 of the garment, and a second hydrophobic extension sheet 52 is disposed at the opposite waist region 28. A material which has been found to function well for extension sheets is 0.4 to 0.6 ounce per square yard (osy) spunbound hydrophobic polypropylene. Extension sheets 50, 52 are substantially similar, and thus only sheet 50 will be described in detail.

Referring to FIGS. 1 and 2, and describing the disposition of extension sheet 50, it extends laterally of the diaper over a major portion of waist region 26. It has an outer edge margin portion 50a which overlies and is secured to the surface of waistband 44 opposite the surface of the waistband secured to back sheet 12. Opposite ends of the extension sheet, such as noted at 50b, extend beyond the ends of waistband 44 and are secured, as by adhesive, to backing sheet 12.

An opposite edge margin portion 50c of extension sheet 50 is interposed between pad 16 and back sheet 12, and is secured therebetween, by adhesive. The intermediate portion 50d of extension sheet 50 extends in a substantially evenly curved contour from the region adjacent the pad to the waistband.

In the illustrated embodiment of the invention, end margin portions 14a, 14b of the liner sheet which are wrapped around the ends of the pad extend inwardly from the end edge of the pad a distance of at least 0.25 inch. The end edges of the pad are spaced inwardly from the waistbands a distance of at least one-half inch. The intermediate portions 50d, 52d of the extension sheets extend in substantially even, or smooth, contours, or curves, between their portions underlying the pad and their portion overlying the waistbands.

Referring to FIGS. 3, 4 and 5, a simplified side elevation view of a method for assembling such a disposable absorbent garment is illustrated. Referring first to FIG. 3, the parts are shown in exploded view, with back sheet 12 lying in a planar position, waistband pieces 44, 46 overlying opposite ends of the back sheet, and outer edge margin portions 50a, 52a of extension sheets 50, 52 overlying the waistband pieces. Pad 16 is spaced above the back sheet and inner edge margin portions 50c, 52c of extension sheets 50, 52. The liner sheet 14 is spaced above the pad.

The liquid impervious back sheet 12 is formed to have the generally hourglass-shaped configuration illustrated in FIG. 1 with opposed laterally extending waist regions 26, 28 at opposite ends thereof and an intermediate crotch region. The back sheet is positioned with its inner side facing up. The waistband pieces 44, 46 are secured to opposite waist regions of the back sheet, either by adhesive placed between the waistband pieces and the back sheet, or by heat bonding.

The outer marginal edge portions 50a, 52a of the hydrophobic extension sheets 50, 52 are placed over the upper side surfaces of the waistbands 44, 46 with remainder portions of the extension sheets extending toward the crotch region of the back sheet. These extension sheets are secured to the waistband and to the inner side of the underlying back sheet, as by adhesive or heat bonding.

The absorbent pad 16, having a length shorter than the distance between the opposed waistbands is formed as illustrated. The liquid pervious liner sheet 14 is placed atop pad 16 and its end margin portions 14a, 14b are wrapped around end edges 16a, 16b of the pad and terminate adjacent the underlying, or opposite, face of the pad. The pad and liner sheet combination then is secured by adhesives to the crotch region of the inner face of the back sheet, with the end edges 16a, 16b of the pad spaced inwardly from the waistbands and overlying the inner end margin portions 50c, 52c of the extension sheets. As has been stated previously, the end margin portions of the liner sheet are wrapped to extend at least 0.25 inch inwardly from the opposite end edges of the pad. The pad is dimensioned so that its end edges 16a, 16b are positioned at least one-half inch from the inner edges 44a, 46a of the waistbands.

The component parts of the absorbent garment may be secured together by lines of adhesive applied to the various parts during the assembly operation, or by a variety of heat or ultrasonic welding procedures.

The liner sheet 14 is of a material which may have a surfactant applied thereto to make it hydrophilic. By having only minor portions 50c, 52c of extension sheets 50, 52 contacting the hydrophilic liner sheet, there is only minimal opportunity for surfactant materials to transfer from the liner sheet to the extension sheets which might render the extension sheets hydrophilic. The extension sheets thus retain their hydrophobic characteristics to inhibit lateral transfer of liquids from the area of the pad toward the waist regions of the garment.

Having the hydrophilic liner sheet wrap back and under the outer edge of the absorbent pad also serves to direct any wicking flow of liquids along the surface of the hydrophilic material back toward the center of the diaper, rather than laterally toward the waist regions of the garment.

The hydrophobic extension sheets provide a barrier between the pad and liner sheet combination and the waist region of the garment to inhibit transmission of fluids toward the waist region.

Not only do the hydrophobic extension sheets 50, 52 provide the benefits set out above, but they also provide covers for the elastic waistbands and for glue lines that may exist on the inner side of the back sheet for fabrication purposes. Thus the extension sheets provide not only liquid flow inhibiting separation between the end of the absorbent pad and liner sheet and the waist region, but also provide a comfort benefit by separating the wearer from glue lines. Also, it prevents rubbing between the elastic waistbands and the wearer's body. Further, the even contour portions 50d, 52d of the extension sheets provide comfortable contact for the wearer.

Basically, without intending to limit the present invention, the invention provides a disposable absorbent garment that is especially useful to minimize leakage around the waist region of the user. The improved containment characteristics are provided by the extension sheets at opposite ends, or waist regions, of the garment which overlie the elastic waistband pieces, and extend to positions where they underlie the absorbent pad. The liner for the absorbent pad wraps around the ends of the pad to provide wicking of liquids back and into the center of the garment which would otherwise attempt to move, or flow, outwardly through the waist regions of the garment. Since the extension sheets are hydrophobic there is little chance that they will provide a route for liquids to migrate from the center of the garment to the waistband region. This provides a substantially dry cover for the waistband region and contains materials within the desired area of the garment.

While a particular embodiment of the present invention has been illustrated and described herein, it should be obvious to those skilled in the art that variations and modifications are possible without departing from the spirit of the invention as set out in the appended claims.

I claim:

1. A disposable absorbent garment comprising
   a liquid impervious back sheet having inner and outer sides, opposed transverse waist regions, and a crotch region therebetween,
   an elongate waistband secured to and extending along the inner side of a waist region of the back sheet,
   an absorbent pad overlying the inner side of said crotch region of the back sheet, said pad having an end edge spaced inwardly from said waistband,
   a liquid pervious liner sheet overlying said pad and having an end margin portion wrapped around said end edge of the pad and terminating between the pad and back sheet, and
   a hydrophobic extension sheet extending between said pad and waistband having a first portion overlying said waistband and a second portion interposed between said pad and back sheet.

2. The garment of claim 1, wherein said second portion of said extension sheet is interposed between an end margin portion of the liner sheet and said back sheet.

3. The garment of claim 2, wherein said extension sheet extends in a substantially even contour from said pad to said waistband.

4. The garment of claim 1, wherein said second portion of the extension sheet comprises an end margin which terminates adjacent said wrapped end margin portion of the liner sheet.

5. The garment of claim 1, wherein said end margin portion of the liner sheet extends inwardly from said end edge of the pad a distance of at least 0.25 inch.

6. The garment of claim 1, wherein said end edge of the pad is spaced inwardly from the waistband a distance of at least one half inch.

7. The garment of claim 1, wherein said extension sheet spans substantially the full length of the waistband.

8. The garment of claim 1, wherein one side of said waistband is secured to the back sheet, said first portion of the extension sheet is secured to the opposite side of said waistband, and said second portion of the extension sheet is secured to said back sheet in a region spaced inwardly from said waistband.

9. The garment of claim 1, wherein said waistband comprises an elongate strip of cushioning material.

10. The garment of claim 1, wherein said extension sheet comprises a sheet of non-woven hydrophobic fibers.

11. A disposable absorbent garment comprising
    a liquid impervious back sheet having inner and outer sides, opposed transverse waist regions, and a crotch region therebetween,
    an elongate waistband secured to and extending along the inner side of a waist region of the back sheet, an absorbent pad overlying the inner side of said crotch region of the back sheet, said pad having an end edge spaced inwardly from said waistband,
    a liquid pervious liner sheet overlying said pad and having an end margin portion wrapped around said end edge of the pad and terminating between the pad and back sheet, and
    a hydrophobic extension sheet extending in a substantially even contour between said pad and waistband having a first portion overlying said waistband and a second portion interposed between said pad, end margin portion of the liner sheet and back sheet, with said extension sheet spanning substantially the full length of the waistband.

12. The garment of claim 11, wherein said first portion of said extension sheet is secured to said waistband and said second portion of the extension sheet is secured to said back sheet in a region spaced inwardly from said waistband.

13. The garment of claim 11, wherein said end margin portion of the liner sheet extends inwardly from said end edge of the pad a distance of at least 0.25 inch, and said second portion of the extension sheet comprises an end margin which terminates adjacent said end margin portion of the liner sheet.

14. The garment of claim 11, wherein said end edge of the pad is spaced inwardly from the waistband a distance of at least one half inch.

15. The garment of claim 11, wherein said waistband comprises an elongate strip of cushioning material.

16. A method for producing a disposable absorbent garment comprising the steps of forming a liquid impervious back sheet having an inner side, opposed laterally extending waist regions, and a crotch region intermediate said waist regions, attaching one side surface of an elongate waistband to the inner side of a waist region of the back sheet, placing a portion of a hydrophobic extension sheet over the opposite side surface of said waistband with remainder portions of the extension sheet extending toward the crotch region of the back sheet and securing the extension sheet in place, providing an absorbent pad having a length shorter than the distance between the opposed waist regions of the back sheet, overlying one face of the pad with a liquid pervious liner sheet with an end margin portion of the liner sheet wrapping around an end edge of the pad and terminating adjacent the opposite face of the pad, and securing the combined pad and liner sheet to the crotch region of the inner face of the back sheet with said end edge of the pad spaced inwardly from the waistband and overlying a portion of the extension sheet.

17. The method of claim 16, wherein in the step of overlying the pad with a liquid pervious liner sheet said end margin portion of said liner sheet is wrapped to extend at least 0.25 inch inwardly from the edge of the pad.

18. The method of claim 16, wherein in the step of securing the combined pad and liner sheet to the back sheet said end edge of the pad is positioned at least one half inch from the waistband.

19. The method of claim 16, which further comprises the step of securing a portion of the extension sheet spaced inwardly from the waistband to the inner face of the back sheet.

20. The method of claim 16, wherein in the step of placing a portion of a hydrophobic extension sheet over said waistband the extension sheet is dimensioned and positioned to span substantially the full length of the waistband and a portion of the extension sheet is secured to the waistband.

* * * * *